United States Patent [19]

Parnham

[11] Patent Number: 4,757,063
[45] Date of Patent: Jul. 12, 1988

[54] PROCESS FOR THE TREATMENT OF DISEASES CAUSED BY OXIDATIVE STRESS

[75] Inventor: Michael J. Parnham, Pulheim, Fed. Rep. of Germany

[73] Assignee: A. Nattermann & CIE. GmbH, Cologne, Fed. Rep. of Germany

[21] Appl. No.: 49,728

[22] Filed: May 12, 1987

[30] Foreign Application Priority Data

May 20, 1986 [DE] Fed. Rep. of Germany ....... 3616923

[51] Int. Cl.$^4$ .............................................. A61K 31/33
[52] U.S. Cl. .................................................... 514/183
[58] Field of Search ......................................... 514/183

[56] References Cited

U.S. PATENT DOCUMENTS 4,352,799 10/1982 Renson et al. ...................... 424/244

OTHER PUBLICATIONS

R. Weber et al., Bulletin de la Soc. Chim. de France 1976 (7/8) pp. 1124–1126.
H. Sies, Oxidative Stress, 1985, pp. 1–8.
R. C. Allen et al., Biochemical and Biophysical Research Communications, vol. 47, No. 4, pp. 679–684 (1972).
Knox Van Dyke et al., Microchemical Journal 25, 514–523 (1980).
David A. Hume et al., Biochem. J. (1981) vol. 198, pp. 661–667.Enrique Cadenas et al., Biochem. J. (1980) vol. 192, pp. 303–309.
Alberto Boeris et al., Federation Proceedings, vol. 40, No. 2, (1981) pp. 195–198.
Robert C. Young et al., The New England Journal of Medicine, vol. 305, No. 3, (1981), pp. 139–153.
Thomas R. Tritton et al., Science, vol. 217, (1982), pp. 248–250.
Albrecht Wendel, Methods in Enzymology, vol. 77, (1981), pp. 325–333.

*Primary Examiner*—Stanley J. Friedman
*Attorney, Agent, or Firm*—Pearne, Gordon, McCoy & Granger

[57] ABSTRACT

The invention is related to a process for the treatment of diseases caused by oxidative stress in human beings comprising administering to said human being a pharmaceutical preparation comprising 2-phenyl-1,2-benzisoselenazol-3(2H)-one as active agent in an amount of 10 to 2000 mg per day.

1 Claim, No Drawings

PROCESS FOR THE TREATMENT OF DISEASES CAUSED BY OXIDATIVE STRESS

The invention relates to a new use of 2-phenyl-1,2-benzisoselanzol-3(2H)-one (generic name: Ebselen), i.e. for the therapy of diseases caused by oxidative stress and for pharmaceutical preparations containing this active agent for this purpose.

2-Phenyl-1,2-benzisoselanzol-3(2H)-one is a known compound which is used for the treatment of rheumatic diseases (U.S. Pat. No. 4,352,799) and is produced according to the process of R. Weber, M. Renson, *Bulletin de la Soc. Chim. de France* 1976 (7/8), pgs. 1124–1126 by reaction of 2-methylseleno-2-phenyl-benzamide with phosphorous pentachloride and subsequent hydrolysis.

OXIDATIVE STRESS

All aerobic organisms use oxygen for the production of energy. However, there are many indications that the advantages of using oxygen are associated with the risk that the oxidative processes may also cause injury to the treated beings too. Various active oxygen metabolites participate in such oxidative processes and at the same time attack the various classes of biological materials. Almost all classes of chemical compounds are subject to oxidative impairment by such oxygen compounds. For instance, the nucleic acids, proteins and free amino acids, lipids and hydrocarbon compounds are influenced by the oxygen toxicity. The human organism has a most refined, widespread and therefore obviously very important system to balance its oxidative and antioxidative processes (see H. Sies, *Oxidative Stress*, pgs. 2–4, 1985).

The shifting of this balance towards oxidative processes may have two reasons:

1. overburden of the antioxidative system because of the production of an active oxygen metabolite and/or
2. insufficiency of the antioxidative system.

The results have been summarized by the expression "oxidative stress". It is known today that such a shifting of the balance may be caused by many different diseases, in particular the inflammatory diseases such as hepatitis, CNS (Central Nervous System)-diseases as epilepsy or Parkinson's disease, diseases of the pulmonary organs such as asthma, psoriasis, side-effects of anticancer agents, chemicals such as paraquat and side-effects of radiation as well as diseases of the coronary circulation such as cardiac infarction.

It has been surprisingly found that 2-phenyl-1,2-benzisoselenazol-3(2H)-one is a useful compound in the therapy of diseases caused by oxidative stress as shown by the following in vitro tests.

1. Chemiluminescence

The generation by activated cells of reactive oxygen species is frequently determined by the measurement of chemiluminescence (CL). The radical species formed react with a photon-producing chemical (f.i. Luminol) and the resulting light emission is measured with a photocell. Chemiluminescence is detectable as a result of the stimulation of leucocytes and is a measure of their oxidative cytotoxic activity (see R. C. Allen et al., *Biochem. Biophys. Res. Commun.* 47, 679, 1972). It is also generated by stimulated human platelets (see K. van Dyke et al., *Microchem. J.* 25, 514, 1980) and lymphocytes (D. A. Humes et al., *Biochem. J.* 198, 661, 1981) as well as by liver, brain and lung tissue submitted to oxidative stress (see E. Cadenas et al., *Biochem. J.* 192, 303, 1980; A. Boveris et al., *Fed. Proc.* 40, 195, 1981).

Consequently, chemiluminescence may be considered as a response of a cell or tissue to oxidative stress. It has been shown that Ebselen inhibits chemiluminescence generated from stimulated mouse macrophages (see following Table 1) or from liver microsomes. Consequently, Ebselen is to be considered as an inhibitor of the products of oxidative stress in cells or tissues.

TABLE 1

Inhibition by Ebselen of CL generated by opsonized zymosan or phorbol myristic acetate stimulated mouse peritoneal macrophages in vitro

| Stimulus | Cells ($1 \times 10^5$/ml) | Ebselen Conc. ($\mu$mol/l) | Percent inhibition |
|---|---|---|---|
| Op. Zymosan | Resident macrophages | 0.6 | 12 |
|  |  | 1.8 | 40 |
|  |  | 6.0 | 53 |
|  |  | 18.3 | 97 |
| PMA | C. parvum-activated macrophages | 0.1 | 0 |
|  |  | 1.0 | 17 |
|  |  | 10.0 | 76 |

Thus, Ebselen provides a basis for the therapy of a variety of conditions under which oxidative stress becomes excessive such as irradiation or chemical toxicity.

2. Doxorubicin-induced cell toxicity

Many cytotoxic drugs are used for the therapy of cancer (see. R. C. Young et al., *J. Med.* 305, 139, 1981). Because of their cytotoxicity these compounds produce a wide variety of side-effects. One of these compounds, doxorubicin, is thought to induce side-effects through reactive radical generation (see T. R. Tritton and G. Yee, *Science* 217, 248, 1982). It is shown that Ebselen is an inhibitor of the killing of cells in vitro by doxorubicin (see Table 2). The reference compound catalase, a scavenger of $H_2O_2$, is also effective.

TABLE 2

Inhibition of cell killing caused by doxorubicin by Ebselen in MCF-7 cells

| | Percent of control (without Dox) | | |
|---|---|---|---|
| Compound | Dox 0.4 $\mu$mol/l | Dox 0.5 $\mu$mol/l | Dox 0.75 $\mu$mol/l |
| None | 60 | 49 | 42 |
| Ebselen (5 $\mu$mol/l) | — | 74 | — |
| Catalase (3000 U/ml) | 91 | 87 | 69 |

These data indicate that Ebselen is able to protect cells from the damaging effects of radical-inducing chemicals. Since a variety of chemicals including environmental toxins are known to induce oxidative radical stress, the above tests indicate that Ebselen is useful for the therapy of such oxidative stress reactions in general.

3. Diquat-induced cytotoxicity

A compromised isolated hepatocyte system is used to investigate the mechanism of cytotoxicity of diquat, a bipyridylium compound known to undergo redox cycling. Superoxide anious $O_2-$ and $H_2O_2$ are generated within this hepatocyte model as a consequence of the cyclic reduction and oxidation of diquat. Compromised hepatocytes are prepared by pretreatment with 1,3-bis-(2-chloroethyl)-1-nitrosourea to inhibit glutathione reductase activity. The addition of diquat to the compromised hepatocytes rapidly depleted the cellular glutathione levels (GSH), increased the GSSG formation, and produced significant cell death within one hour. Diquat did not alter cellular GSH/GSSG levels, nor did it result in cell death, when added to hepatocytes not pretreated with 1,3-bis-(2-chloroethyl)-1-nitrosourea, demonstrating the importance of the glutathione reductase/peroxidase enzyme system in the protection against diquat-generated $H_2O_2$. The addition of glutathione (GSH) or N-acetyl cysteine to the incubations did not protect the compromised hepatocytes against diquat cytotoxicity. Ebselen, which possesses glutathione peroxidase activity, also failed to protect against cytotoxicity but did inhibit diquat-associated lipid peroxidation. When Ebselen was added in combination with either GSH or N-acetyl cysteine, however, diquat-associated depletion of cellular GSH levels was significantly delayed and cell-death was not apparent until at least the last third of the hour of incubation. These results suggest that Ebselen may also be effective in protecting against diquat and other pathological conditions under which oxidative stress induced by oxygen radicals and hydroperoxides is the underlying process.

4. Lipid peroxidation in vitro

Female adult Wistar rats weighing about 200 g each have been used for the tests. The test animals have been kept at standard conditions, i.e. Altromin feed, usual water for dringing, Makrolon cages, neon-illumination at a rhythm of 12 hours, at 22° C., and at 30% humidity in the air.

The liver is extracted under narcosis with urethane (intraperitoneally 5 ml of a 25% (w/v) aqueous solution per kg of body weight), after the livers have previously been desanguinated and washed in situ with physiological NaCl solution by way of the vena porta. Liver microsomes have been prepared in usual manner by ultracentrifugation.

Freshly prepared microsome suspension was used in all tests. The microsome fraction was suspended in a phosphate buffer solution at pH 7.4. The test on lipid peroxydation stimulated within 1 hour by ascorbic acid, in liver microsomes was effected by means of a standard procedure. The malondialdehyde produced during lipid peroxidation after 1 hour was determined spectrophotometrically. Its concentration is used as an indirect measure for lipid peroxidation. The test products were added as solution in 10 μl of ethanol to the tested samples (5 ml with 5 mg of microsomale protein). This small ethanol concentration has no influence to the lipid peroxidation.

As a control the malondialdehyde concentration resulting from ascorbic acid stimulation is given as 100%. Each sample containing the compounds to be tested is given in relation to this control. A mean value±SEM is calculated from the obtained data. Significant differences are calculated by the t-test according to Students. A difference with a $p<0.05$ is considered as significant. The formation of malondialdehyde stimulated by ascorbic acid after 1 hour (controls) amounted to 84.6±14.7 nM/ml (mean±SEM; n: all controls, normal values, 100% value). When added to each test sample after initiation of of malondialdehyde formation Ebselen in a concentration between 36 and 360 nM per ml of test sample diminished malondialdehyde formation substantially (for 76 to 90%); $p<0.001$ in each cases) at all concentrations of the test compounds.

If added at concentrations between 36 and 360 nM, Ebselen per ml of the test sample 30 minutes before start of the reaction with ascorbic acid, the concentration 36 nM/ml test volume did not prevent the formation of malondialdehyde, while adding 72 and 360 nM per ml of ml test volume resulted in a complete initiation of malondialdehyde formation ($p<0.001$).

Ebselen thus inhibits lipid peroiydation at low concentrations and for quite sure at an early stage of the chain reaction as a radical scavening agent. Therefore, Ebselen is considered to be appropriate to inhibit and treat pathologic conditions caused by an oxidative stress in the form of excess lipid peroxidation.

5. Glutathione peroxidase property

In-vitro-tests showed the ability of 2-phenyl-1.2-benzisoselenazol-3(2H)-one (Ebselen) to catalyse the decomposition of peroxides when being used in the presence of thiols.

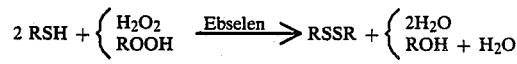

This property of Ebselen is similar to the property of the mammalian enzyme glutathione peroxidase (GSH-Px). Therefore, Ebselen acts as a pseudo-enzyme.

The reactivity of the thiols are measured by the method of A. Wendel (A. Wendel, *Methods in Enzymology* vol. 77, p. 325–333 (1981)). The following pseudo enzyme activity values have been determined by use of gluatathione (GSH) as substrate (1 mmol/l), expressed in glutathione peroxidase units (U) Δ log GSH/min per mol/l selenium as Ebselen;

$1.1 \times 10^6$ with $H_2O_2$
$1.17 \times 10^6$ with t-butylhydroperoxide (t-BuOOH)
$1.7 \times 10^6$ with cumolhydroperoxide (CuOOH).

Under these conditions pure GSH-Px from red cells from cow blood showed an activity of $10^{10}$ U per molar enzyme-bound selenium.

Ebselen and the mammalian seleno-enzyme GSH-Px catalyse the reaction both of inorganic as well as various organic hydroperoxides. Ebselen however differs from the natural enzymes in that the natural enzyme shows a high specifity for GSH as substrate while Ebselen also catalyses the reaction with many other thiols.

Pseudo-enzyme activities for various thiols (t-BuOOH, Ebselen Δ log RSH in place of Δ log GSH)

| glutathion | $1.17 \times 10^6$ |
|---|---|
| cysteine | $2.5 \times 10^6$ |
| N—acetyl-cysteine | $0.47 \times 10^6$ |
| 3-mercaptopropionic acid | $1.05 \times 10^6$ |
| 2-mercapto acidic acid ethylester | $3.8 \times 10^6$ |
| erythro-1.4-dimercapto-2.3-butandiole | $4.6 \times 10^6$ |

As follows from the tests, Ebselen may be used as a valuable prophylactic agent and/or therapeutic agent with diseases cause by oxidative stress, such as with diseases of the bronchial system including the adult respiratory distresssyndrom (ARDS) or side effects of anticancer compounds, with CNS diseases such as epilepsy or Parkinson's disease, with radiation damage or toxic effects of chemical compounds such as paraquat, with liver complaints, with heart-circulation-diseases such as heart infarction or with psoriasis.

The present invention is further related to pharmaceutical preparations containing Ebselen as active agent. The pharmaceutical preparations according to the present invention are for enteral as well as oral or rectal as well as parenteral administration. They contain Ebselen as a pharmaceutically active agent alone or together with usual pharmaceutically applicable carrier materials. Preferably, the pharmaceutical preparation contains the active agent as a single dose form in accordance with the desired treatment, such as tablets, dragees, capsules, suppositories, granulates, solutions, emulsions or suspensions. The dosages of Ebselen in general are between 10 and 2000 mg per day, preferably between 30 and 300 mg per day and may be administered as a single dose or in several partial doses, preferably in 2 or 3 partial doses per day.

The production of the pharmaceutical preparations in accordance with the present invention is illustrated by the following examples.

EXAMPLE 1

| Tablets | |
| --- | --- |
| 2-Phenyl-1.2-benzisoselenazol-3(2H)—one | 30 mg |
| lactose | 150 mg |
| cristalline cellulose | 50 mg |
| calcium carboxymethylcellulose | 7 mg |
| magnesium stearate | 3 mg |

The above components are mixed and compressed to tablets in usual manner. If desired, the pressed crude tablets are covered in usual manner.

EXAMPLE 2

| Tablets | |
| --- | --- |
| 2-Phenyl-1.2-benzisoselenazol-3(2H)—one | 50 mg |
| microcristalline cellulose | 150 mg |
| Cutina ® HR | 15 mg |
| Hydroxypropyl methyl cellulose phthalate | 20 mg |

EXAMPLE 3

| Capsules | |
| --- | --- |
| 2-Phenyl-1.2-benzisoselenazol-3(2H)—one | 30 mg |
| lactose | 102 mg |
| cristalline cellulose | 56 mg |
| colloidal siliciumdioxide | 2 mg |

The above components are mixed in usual manner, granulated and filled into capsules of hard gelatine.

EXAMPLE 4

| Capsules | |
| --- | --- |
| 2-Phenyl-1.2-benzisoselenazol-3(2H)—one | 50 mg |
| talkum | 5 mg |
| Aerosil 200 | 10 mg |

What I claim is:

1. Process for the treatment of diseases caused by oxidative stress in human beings comprising administering to said human being a compound comprising 2-phenyl-1.2-benzisoselenazol-3(2H)-one as active agent in an amount of 10 to 2000 mg per day.

* * * * *